US011820758B2

(12) United States Patent
De Rosa et al.

(10) Patent No.: US 11,820,758 B2
(45) Date of Patent: Nov. 21, 2023

(54) NEK6 KINASE INHIBITORS USEFUL FOR THE TREATMENT OF SOLID TUMORS

(71) Applicants: CONSIGLIO NAZIONALE DELLE RICERCHE, Rome (IT); MOLIPHARMA S.R.L., Campobasso (IT)

(72) Inventors: Maria Cristina De Rosa, Rome (IT); Davide Pirolli, Rome (IT); Giovanni Scambia, Campobasso (IT); Daniela Gallo, Campobasso (IT); Marco Petrillo, Campobasso (IT); Marta De Donato, Campobasso (IT); Benedetta Righino, Campobasso (IT)

(73) Assignees: CONSIGLIO NAZIONALE DELLE RICERCHE, Rome (IT); MOLIPHARMA S.R.L., Campobasso (IT)

( * ) Notice: Subject to any disclaimer, the term of this patent is extended or adjusted under 35 U.S.C. 154(b) by 0 days.

(21) Appl. No.: 17/045,028

(22) PCT Filed: Apr. 2, 2019

(86) PCT No.: PCT/IB2019/052688
§ 371 (c)(1),
(2) Date: Oct. 2, 2020

(87) PCT Pub. No.: WO2019/193494
PCT Pub. Date: Oct. 10, 2019

(65) Prior Publication Data
US 2021/0147395 A1 May 20, 2021

(30) Foreign Application Priority Data

Apr. 3, 2018 (IT) .................. 102018000004172
Apr. 3, 2018 (IT) .................. 102018000004177

(51) Int. Cl.
| | | |
|---|---|---|
| *C07D 405/06* | (2006.01) | |
| *C07D 471/04* | (2006.01) | |
| *A61K 33/243* | (2019.01) | |
| *A61K 31/337* | (2006.01) | |
| *A61K 45/06* | (2006.01) | |

(52) U.S. Cl.
CPC ......... *C07D 405/06* (2013.01); *C07D 471/04* (2013.01); *A61K 31/337* (2013.01); *A61K 33/243* (2019.01); *A61K 45/06* (2013.01)

(58) Field of Classification Search
None
See application file for complete search history.

(56) References Cited

FOREIGN PATENT DOCUMENTS

| WO | WO-2011094708 A2 | 8/2011 |
| WO | WO-2019193494 A1 | 10/2019 |

OTHER PUBLICATIONS

Tu et al., Ultrasonics Sonochemistry (2008), 15(3), pp. 217-221.*
Cai, C.W., et al., "Hepatitis B virus replication is blocked by a 2-hydroxyisoquinoline-1,3(2H,4H)-dione (HID) inhibitor of the viral ribonuclease H activity," *Antiviral Research* 108:48-55, Elsevier BV, Netherlands (2014).
Ceylan, S., et al., "Inductive heating with magnetic materials inside flow reactors," *Chemistry—A European Journal* 17(6):1884-1893, Wiley-VCH Verlag, United Kingdom (2011).
Gentile, F., et al., "New design of nucleotide excision repair (NER) inhibitors for combination cancer therapy," *Journal of Molecular Graphics and Modelling* 65:71-82, Elsevier Science, United States (2016).
International Search Report and Written Opinion for International Application No. PCT/IB2019/052688, European Patent Office, Netherlands, dated Aug. 29, 2019, 18 pages.
Nassirpour, R., et al., "Nek6 mediates human cancer cell transformation and is a potential cancer therapeutic target," *Molecular Cancer Research* 8(5):717-728, American Association for Cancer Research Inc., United States (2010).
Shaabani, A., et al., "A green one-pot three-component cascade reaction: the synthesis of 2-amino-5,8-dihydro-3H-pyrido[2,3-D]pyrimidin-4-ones in aqueous medium," *Molecular Diversity* 21(1):147-153, Springer, Netherlands (2017).
Srinivasan, P., et al., "Discovery of novel inhibitors for Nek6 protein through homology model assisted structure based virtual screening and molecular docking approaches," *The Scientific World Journal* 2014:967873, Hindawi Ltd., Egypt (2014).
Tu, S., et al., "An efficient synthesis of pyrido[2,3-d]pyrimidine derivatives and related compounds under ultrasound irradiation without catalyst," *Ultrasonics: Sonochemistry* 15(3):217-221, Elsevier BV, Netherlands (2007).

* cited by examiner

*Primary Examiner* — Brian J Davis
(74) *Attorney, Agent, or Firm* — STERNE, KESSLER, GOLDSTEIN & FOX P.L.L.C.

(57) ABSTRACT

The mitotic kinases regulating the dynamics of centrosomes and the functions of the mitotic spindle are potential targets for the antitumour therapy. In the present invention some molecules with inhibitory activity on NEK6 have been identified. The present invention relates to such molecules and to the compositions including them for use as inhibitors of NEK6 in a method of treatment of tumours both in monotherapy and in combinations with other drugs.

12 Claims, 3 Drawing Sheets

NEK6 KINASE INHIBITORS USEFUL FOR THE TREATMENT OF SOLID TUMORS

TECHNICAL FIELD OF THE INVENTION

The mitotic kinases regulating the dynamics of centrosomes and the functions of the mitotic spindle are potential targets for the antitumour therapy. In the present invention some molecules with inhibitory activity on NEK6 have been identified. The present invention relates to such molecules and to the compositions including them for use as NEK6 inhibitor in a method of treatment of tumours both in monotherapy and in combination with other drugs.

STATE OF PRIOR ART

NEK6 is a serine threonine protein kinase belonging to the family of "NIMA-related kinase". This family comprises eleven proteins (NEK1-NEK11), involved in the progression of the cell cycle and/or in the organization of the microtubules. The protein levels and the catalytic activity of NEK6 increase during mitosis.

In particular, NEK6 seems to be requested in the separation of centrosomes and in the metaphase-anaphase transition of the cell cycle wherein it has a role in maintaining the mitotic spindle (Fry A M J, Cell Sci. 2012; 125:4423-33). Previous studies demonstrated that the inhibition of NEK6 activity, through RNA silencing or use of inactive mutants for the kinase activity, would determine the mitotic stop and apoptosis (Belham C et al. J Biol Chem. 2003; 278:34897-909; Nassirpour et al. Mol Cancer Res. 2010; 8:717-28). It was further reported that NEK6 represents a direct target of the checkpoint of damage to DNA (Lee M Y et al. Cell Cycle. 2008; 7:2705-9). In line with these data, during the last years experimental evidence has consolidated to support a role of NEK6 in tumorigenesis. Several types of solid tumours over-express NEK6, thereamong liver, stomach, breast, colon-rectum, lung, larynx, ovary and prostate (Nassirpour et al. Mol Cancer Res. 2010; 8:717-28; De Donato et al. Am J Cancer Res. 2015; 5:1862-77). NEK6 further represents an independent negative prognostic factor in hepatic carcinoma (Cao X et al. Pathol Oncol Res. 2012; 18:201-7) and ovarian carcinoma (De Donato et al. Am J Cancer Res. 2015; 5:1862-77; patent WO2015/006262 A1), as well as a prognostic and diagnostic biomarker in the tumour of colon-rectum (Gerceker E. et al. Oncol Rep. 2015; 34:1905-14).

The role of NEK6 in the tumour pathogenesis was demonstrated in several human tumour cell lines wherein the expression levels correlate with aggressiveness of cells. The over-expression of NEK6 is capable of promoting the anchorage-independent growth, whereas the functional depletion, by means of silencing of mRNA or by means of the expression of a dominant inactive kinase mutant, annuls such effect, by inducing apoptosis in several lines of human carcinoma, but not in fibroblasts (Nassipour et al. Cancer Res. 2010; 8:717-28). NEK6 results to be also a powerful inhibitor of senescence induced by p53 (Jee H J et al. Cell Cycle. 2010; 9:4703-10). The patent application US2005216961A1 describes the use of several kinases, thereamong NEK6, in the prognosis and screening of new molecules useful in the treatment of different tumours.

NEK6 then is an important therapeutic target for the development of antitumour drugs (Dominguez-Brauer C. et al. Mol Cell. 2015; 60:524-36). The currently used antitumour drugs have the disadvantage of not being selective for the malignant cells. Therefore, the drugs used in past designated to stop specifically the cell cycle during mitosis, gave limited clinical results due to the low therapeutic index linked to the cytotoxicity on the not tumour cells (Dominguez-Brauer C. et al. Mol Cell. 2015; 60:524-36). With the purpose of developing customized therapies in the treatment of tumours it is important to identify new drugs with selective activity against tumour cells. Such drugs could be used alone or in association to the already used first-line therapies or in subsequent therapeutic lines. From this perspective, the NEK kinases, which play a critical role for organizing the microtubules and carrying out the mitosis, represent emerging targets interesting for the development of compounds to be used in association with antitumour drugs (Dominguez-Brauer et al 2015). The important result described by Nassirpour and colleagues (Mol Cancer Res. 2010; 8:717-28) shows that the inhibition of NEK6 induces apoptosis in several cell lines of human carcinoma, but not in the normal primary cell lines, by confirming the importance of the development of selective inhibitors of this protein in the development of new antitumour therapies.

SUMMARY THE INVENTION

The serine threonine protein kinase NEK6 represents an important therapeutic target for the development of new drugs against tumour.

The present invention arises from the search for compounds capable of inhibiting NEK6. First of all, the capability of inhibiting in vitro the kinase activity of NEK6 was examined in several inhibition assays and subsequently the cytotoxic activity of such inhibitors on different tumour cell lines of human origin was demonstrated. Moreover, the compound C8 according to the present invention was assayed in combination with other chemotherapeutic drugs on a line of ovarian carcinoma by showing a synergic effect. Two families of compounds capable of inhibiting NEK6 and of inhibiting the growth of tumour cell lines were thus detected. The compounds identified by the present invention could have the additional advantage of improving the therapeutic effectiveness and reducing the toxic effects. The inhibition of NEK6 activity, in fact, could determine a selective cytotoxic effect on the neoplastic cells and not on the normal cells.

Therefore, the invention relates to the compounds provided with inhibition activity of NEK6 protein having general formula selected from the structure formulas (A) or (B) as herein defined their enantiomers, tautomers salts, and the use thereof in the treatment of a tumour.

The present invention further relates to the compounds having general formula selected from the structure formulas (A) or (B) as herein defined for use as inhibitors of NEK6 protein in a method of treatment, in particular in a method of treatment of a tumour.

The present invention further relates to pharmaceutical compositions comprising the structure formulas (A) or (B) as herein defined and pharmaceutically suitable excipients.

The present invention further relates to pharmaceutical compositions comprising the structure formulas (A) or (B) as herein defined and pharmaceutically suitable excipients and one or more additional chemotherapeutic drugs.

The present invention further relates to kit comprising the compounds having general formula selected from the structure formulas (A) or (B) as herein defined and one or more additional chemotherapeutic drugs and use thereof in a method of treatment of a tumour.

The present invention further relates to processes for the preparation of the compounds having general formula selected from the structure formulas (A) or (B) as herein defined.

DESCRIPTION OF THE FIGURES

FIG. 2 represents the molecules identified with inhibitory activity on NEK6 by using LANCE-Ultra NEK6 kinase assay (PerkinElmer). The curves represent the % of NEK6 activity depending upon the inhibitor concentration. A) The compound 8 (ZINC05007751) is capable of inhibiting the NEK6 activity with I050=3.4±1.2 μM; B) the compound 21 (ZINC04384801) inhibits NEK6 at I050=2.6±0.05 μM. The IC50 value derives from the average of IC50s of 4 independent experiments±SEM. Each point of the curve represents the average of a triplicate±SEM of a representative experiment.

DETAILED DESCRIPTION OF THE INVENTION

Figure 1:
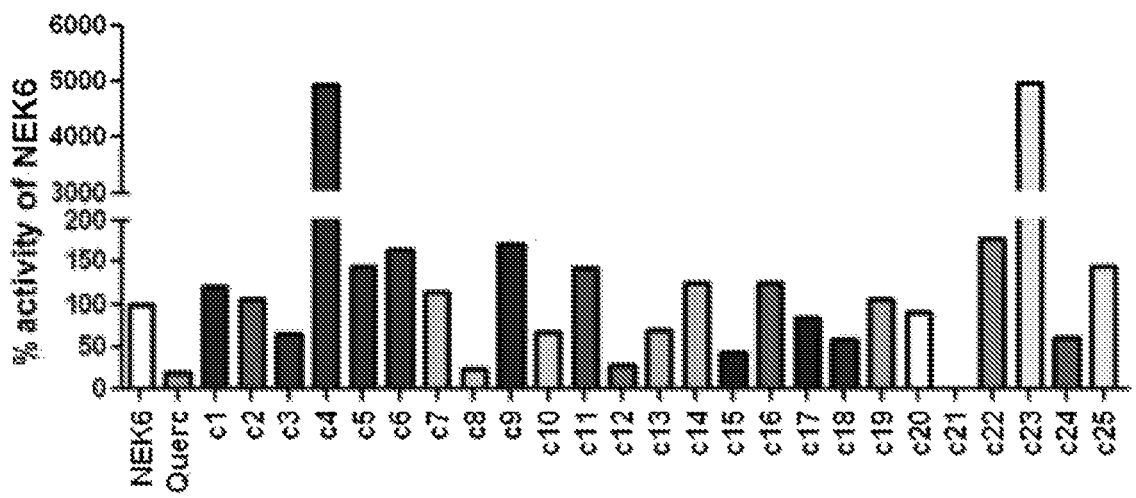
FIG. 1. NEK6 activity inhibition. Bar graph representing the results of the screening of several compounds at 30 μM by using LANCE-Ultra NEK6 kinase assay (PerkinElmer) incubated with 4 nM NEK6, 50 nM ULight-p70 S6K Peptide and 100 μM ATP for 90 minutes at room temperature. As control inhibitor quercetin was used. The most active compounds are those of formula A and B exemplified as compound C8 and C21.

The compounds of the invention are compounds which have in common the same pharmacological activity, that is the inhibition of NEK6 protein, in particular of human NEK6 protein (code in data bank UniProtKB-Q9HC, NEK6_Human). The invention relates to the compounds having general formula selected from formula (A) or (B) shown hereinafter.

A first group of the compounds, the present invention relates to, are compounds of general formula (A)

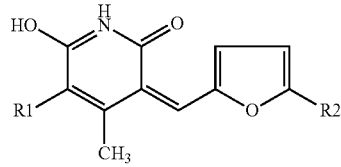

wherein $R^1$ is a substituent selected from anyone of the following groups

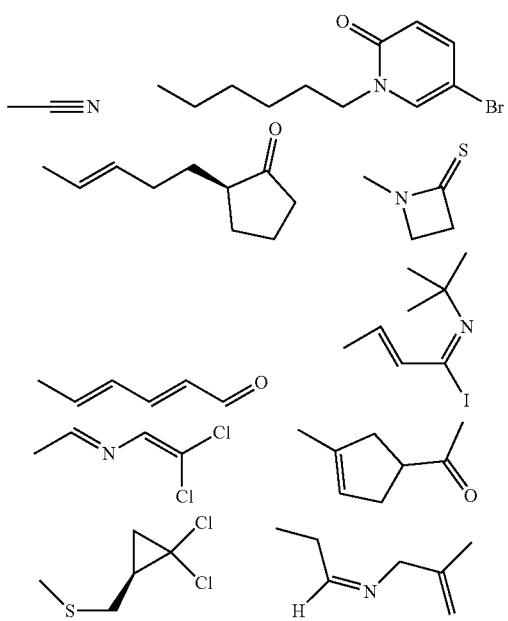

and wherein $R^2$ is a substituent selected from anyone of the following groups:

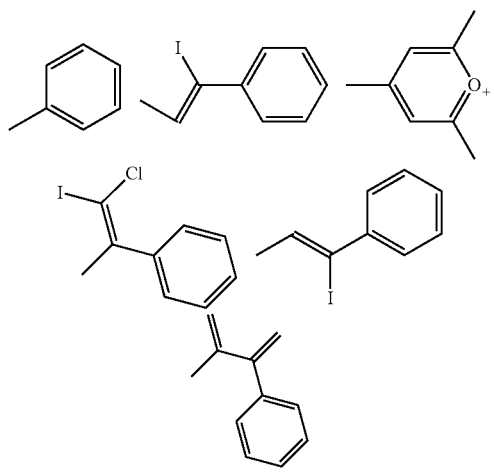

The compound preferably will be selected from one of the following compounds of formula A wherein the substituents are selected according to formulas A1-A15:

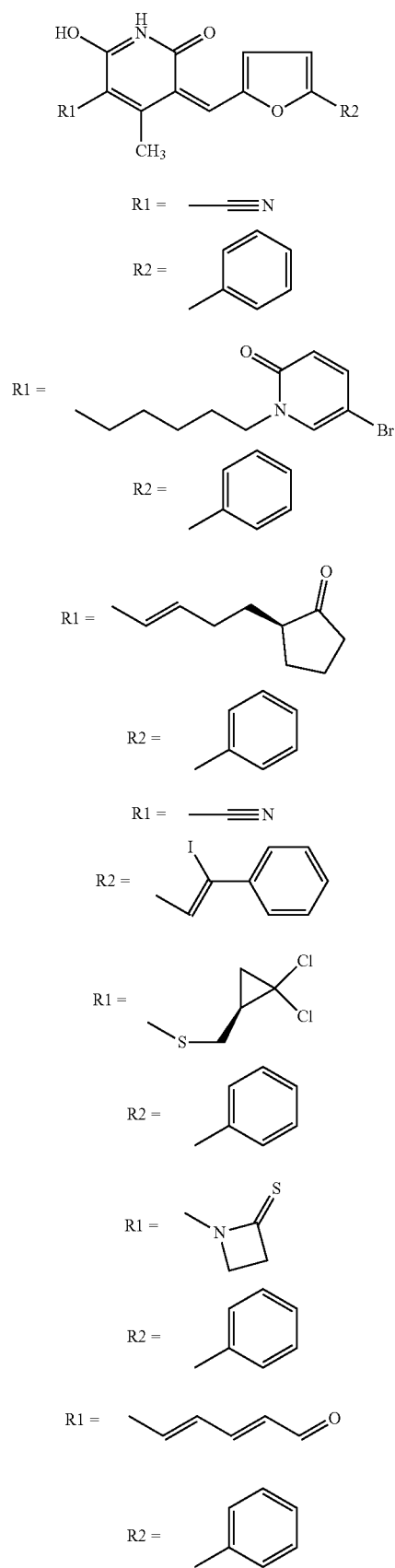

According to a preferred embodiment the compound of formula A is the compound (5Z)-2-hydroxy-4-methyl-6-oxy-5-[(5-phenylfuran-2il)methylidene]-5,6-dihydropyridine-3-carbonitrile identified in the description with the abbreviation C8 and the structure formula thereof is shown hereinafter:

A second group of the compounds the present invention relates to are the compounds of general formula (B):

(B)

wherein R is a substituent selected from the groups B1-B15 shown hereinafter:

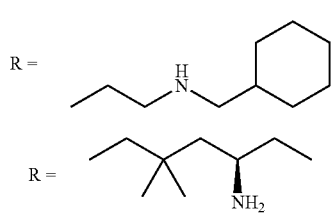

According to a preferred embodiment the compound of formula B is the compound 6-amino-2-phenyl-5,7,9-triaza-tetracycle[8.7.0.0$^3$,$^8$.0$^{11}$,$^{16}$]heptadeca 1(10),3(8),6,11,13,15 hexaene-4, 17-dione identified in the description with the abbreviation C21 and the structure formula thereof is shown hereinafter:

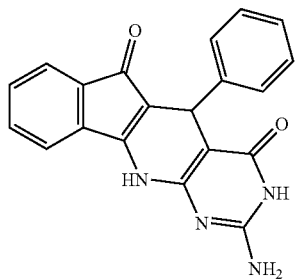 [SMILES: Nc1nc2c(c(=O)[nH]1)C(c1ccccc1)C1=C(N2)c2ccccc2C1=O]

In case for anyone of the herein described compounds a centre of symmetry results, both the racemic mixture and the single (R) or separated (S) enantiomers and a mixture enriched with one of the enantiomers belong to the invention. Even all compounds of formula (A) and (B) described herein in salified form and tautomers thereof belong to the invention.

The invention relates to the above-described compounds (both those of general formula A and B) for use as inhibitors of NEK6 protein in a method of treatment, in particular in a method of treatment of a tumour.

In the present description under the term "inhibitor of NEK6 protein" a substance is meant capable of inhibiting selectively the activity of NEK6 protein. The compounds of the present description could be used with any pathological condition associated to the activity of NEK6 kinase. The compounds of the present description could be used in the treatment of patients affected by cancer, preferably in association to one or more chemotherapeutic drugs, for example Paclitaxel and derivatives thereof, drugs belonging to the class of taxanes, Cisplatin and platinum-based compounds, or other antitumour compounds or biological drugs of potential therapeutic use in the treatment of the tumours. The treated tumour could be the ovarian tumour or other types of tumour such as for example the tumour of the mammary gland, of lung and of colon-rectum.

The invention also relates to the pharmaceutical compositions including one or more compounds of the invention as active ingredient together with a pharmaceutically acceptable excipient and in case additives and stabilizers usual in pharmaceutical industry. Such compositions are suitable for systemic or local use and they can be both in liquid formulation, and in solid or semi-solid formulation or suppository. Examples of liquid formulations are solution, suspension, emulsion, suitable for example for parenteral or local parenteral, oral administration or even in form of spray. Examples of solid formulations are tablets, pills, capsules, granulate, lyophilized, suitable for oral administration. Examples of semi-solid formulations are pastes, creams, gels, ointments, suitable for a topic application. The present invention also relates to a pharmaceutical composition comprising one or more herein described NEK6 inhibitors and a carrier and/or a diluent for use as in a method of treatment of anyone of the herein described conditions to be treated. The composition comprising the NEK6 inhibitor could be oral, parenteral, rectal, transdermal, topic or suitable by other administration route. The compositions for use according to the present invention could be administered by any conventional means available for use together with drugs, or as individual therapeutic agents or in a combination of therapeutic agents. They can be administered alone, but generally administered with a pharmaceutical carrier selected based upon the selected administration route and the standard pharmaceutical practice. The administered dosage, obviously, will vary depending upon known factors, such as the features of pharmacodynamics of the particular agent and upon the administration mode and route thereof; upon age, health and weight of the receiver; upon nature and level of the symptoms, upon the type of concomitant treatment; upon the treatment frequency; and upon the wished effect. It can be provided that a daily dosage of active ingredient is about 0.001 up to 1000 milligrams (mg) per kilogram (kg) of body weight, the preferred dose being 0.1 up to about 30 mg/kg. Dosage forms (compositions suitable for administration) typically include from about 1 mg to about 100 mg of active ingredient per dosage unit. In these pharmaceutical compositions, the active ingredient will be normally present in an amount of about 0.1-95% by weight based upon the total weight of the composition.

One or more herein described inhibitors of NEK6 can be administered by oral route in solid dosage forms, such as capsules, tablets, and powders, or in liquid dosage forms, such as elixirs, syrups and suspensions. It can be administered even by parenteral route, in sterile liquid dosage forms. Capsules of gelatine include the active ingredient and pulverized carriers, such as lactose, starch, cellulose derivatives, magnesium stearate, stearic acid and the like. Similar diluents can be used for preparing pressed tablets. Both tablets and capsules can be manufactured as prolonged-release products to provide continuous release of medication for a period of some hours. Pressed tablets can be coated with sugar or coated with a film to cover any unpleasant taste and protect the tablet from the atmosphere, or coated with enteric coating for the selective disintegration in the gastrointestinal tract. Liquid dosage forms for oral administration can include dyes and flavours to increase the acceptance by the patient. Generally, water, a suitable oil, saline solution, aqueous dextrose (glucose), and solutions of connected sugars and glycols such as propylene glycol or polyethylene glycols are carriers suitable for parenteral solutions. Solutions for parenteral administration preferably include a salt soluble in water of the active ingredient, suitable stabilizing agents and, if required, buffering substances. Antioxidant agents such as bisulphite sodium, sulphite sodium or ascorbic acid, alone or combined, are suitable stabilizing agents. Even citric acid and salts thereof and EDTA sodium are also used. Moreover, parenteral solutions can include preservatives, such as benzalkonium chloride, methyl- or propylparaben, and chlorobutanol. The pharmaceutical compositions according to the present invention apart from the herein described NEK6 inhibitors could include one or more active ingredients, that is pharmacologically active substances, in particular chemotherapeutic drugs. Also, the methods of therapeutic treatment of the above-mentioned pathological conditions are described herein comprising a step for the administration of one of the herein described compounds or the compositions including them. The method could be for the treatment of the tumour and could include a step preceding the administration of the inhibitor wherein a sample of patient is analysed to detect the presence of expression, or not, of NEK6 protein.

All compounds of general formula (A) can be prepared through the synthesis method schematized and described hereinafter and in example 1. Such method is exemplified hereinafter:

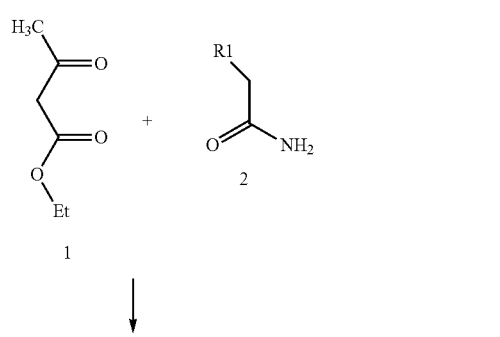

According to a preferred embodiment the reaction conditions of the steps of the method for the preparation of the compounds of general formula (A) will be those shown in the following scheme:

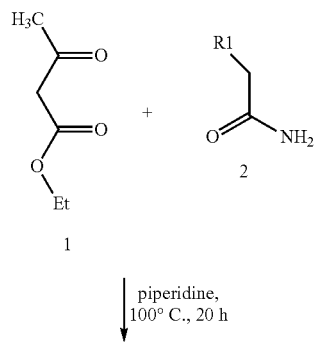

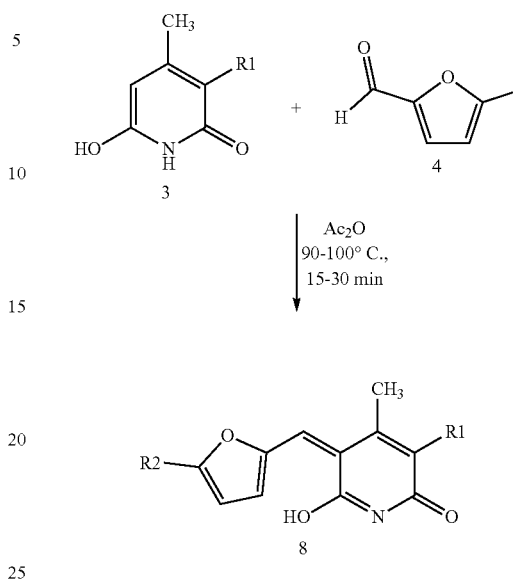

All compounds of general formula (B) can be prepared through the synthesis method schematized and described hereinafter and in the example 2. Such method is exemplified hereinafter:

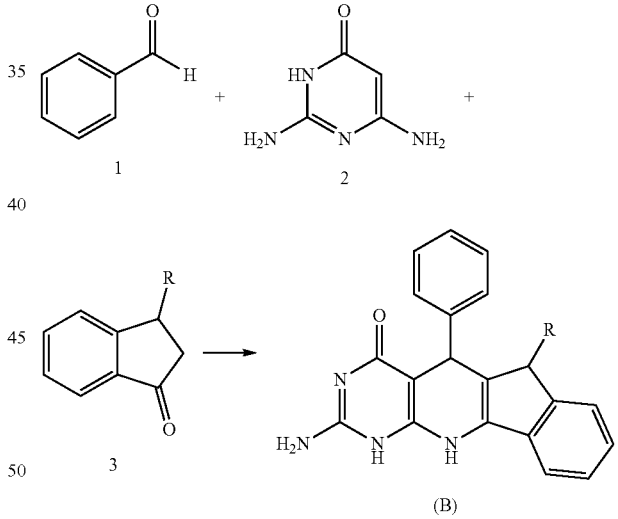

According to a preferred embodiment the reaction conditions of the steps of the method for the preparation of the compounds of general formula (B) will be those shown in the following scheme:

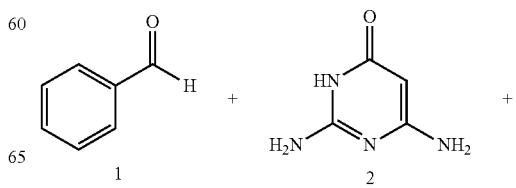

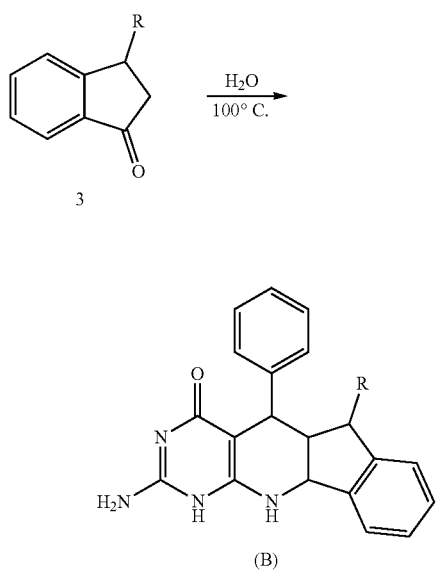

The present invention further relates to kit comprising the compounds having general formula selected from the structure formulas (A) or (B) as herein defined and one or more additional chemotherapeutic drugs and use thereof in a method of treatment of a tumour. The kit could be implemented for example for the oral or parenteral, sequential or simultaneous administration.

The invention will be illustrated in details hereinafter in the following examples, which have exemplifying, but not limitative purpose.

Example 1: synthesis of the compound (5Z)-2-hydroxy-4-methyl-6-oxy-5-[(5-phenylfuran-2il)methylidene]-5,6-dihydropyridine-3-carbonitrile C8. The synthesis took place according to the following scheme

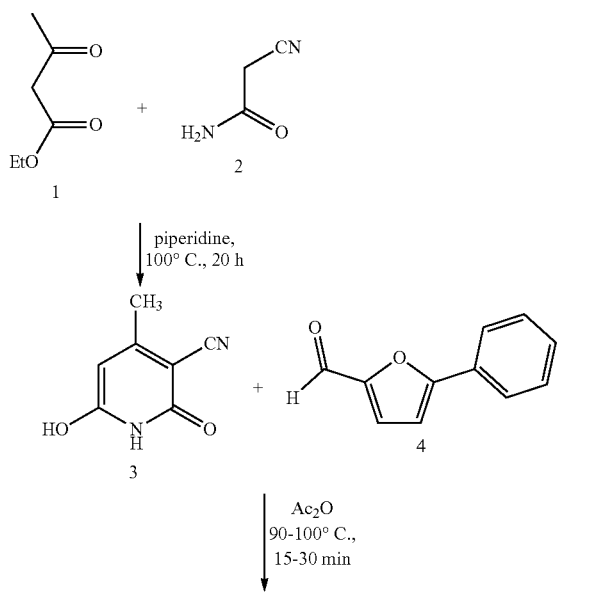

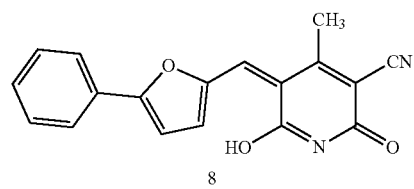

The compounds designated in the scheme as 1, 2 and 4 are commercially available with CAS numbers 141979, 107915 and 13803399, respectively. For the synthesis of example 1 the following references are herein incorporated: Würthner, F. et al. *J. Am. Chem. Soc.* 2001, 123, 2810, Würthner, F. *J. Org. Chem.* 2003, 23, 8943, Renck, D. *J. Med. Chem.* 2013, 56, 8892-8902

Karam A. EI-Sharkawy Eur. Chem. Bull., 2013, 2 (8), 530-537 and W. Cai, C. *Antiviral Research* 2014, 108, 48-55.

Example 2: synthesis of the compound 6-amino-2-phenyl-5,7,9-triaza tetracycle[8.7.0.0$^3$,$^8$.0$^{11}$,$^{16}$]heptadeca-1(10), 3(8),6,11,13,15 hexaene-4, 17-dione C21. The synthesis took place according to the following scheme:

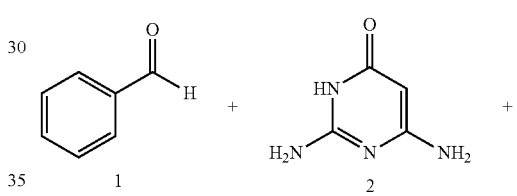

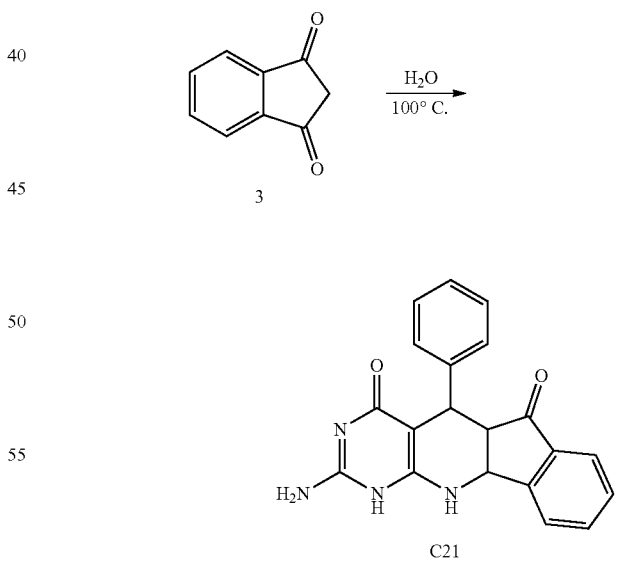

The compounds designated in the scheme as 1 and 3 are commercially available with CAS numbers 100527 and 606235, respectively. The compound 2 can be obtained with the synthesis described in Vyacheslav E. Saraev, *J. Heterocyclic Chem.*, 54, 318 (2017) herein incorporated by reference together with Tu, S.-J. et al *Eur. J. Org. Chem.* 2007,1522.

Experimental Section

1. Materials and methods 1.2 Identification of the Compounds with Inhibitory Activity on NEK6

The compounds in powder (Molport, Riga, LV-1011, Latvia) were dissolved in DMSO 100% at a stock concentration of 10 mM. The fresh compounds were tested initially at a single concentration (30 µM) with LANCE NEK6 Ultra Kinase Assays (Perkin Elmer, Monza (MB)), whereas the remaining solution was aliquoted, kept at −20° C. and used for the enzymatic inhibition curves of the selected compounds. The reaction was performed in 384-OptiPlate™-384 (PerkinElmer #6007290) white plates, by using as reagents the Europium-labeled anti-phospho-p70 S6K (Thr389) Antibody (PerkinElmer #TRF0214), ULight-p70 S6K (Thr389) (PerkinElmer #TRF0126), NEK6 (Carna, Chuo-ku, Kobe, Japan, #05-130), LANCE® Detection Buffer, 10×(PerkinElmer #CR97-100), ATP (Sigma-Aldrich, Saint Louis, U.S.A, #A2383). NEK6, ATP and the compounds were diluted in Kinase Buffer (50 mM HEPES pH 7.5, 1 mM EGTA, 10 mM MgCl2, 2 mM DTT and 0.01% Tween-20), and where necessary DMSO was added to obtain a concentration of 0.3% in the final reaction volume. For the initial screening the compounds were tested at the final concentration of 30 µM, final DMSO 0.3% in kinase buffer and incubated with 4 nM NEK6, 50 nM ULight-p70 S6K Peptide and 100 µM ATP, in a reaction volume of 10 µL for 90 minutes at room temperature. As control inhibitor quercetin (Molport #001-740-557) was used. For the enzymatic inhibition curves, the selected compounds C8 (Molport #002-933-483), C21 (Molport #000-911-820) were diluted serially (dilutions 1:2) from 30 µM to 0.9375 µM (final concentrations: 30 µM; 15 µM; 7.5 µM; 3.75; 1.875 µM; 0.9375 µM in 0.3% DMSO) and incubated under the same conditions. The plates were covered with the film TopSeal™-A film (PerkinElmer #6050195) to avoid evaporation and incubated at room temperature for 90 minutes. The reaction was stopped with 5 µL of EDTA 40 mM prepared in 1×LANCE Detection Buffer (STOP SOLUTION). After 5 minutes at room temperature, 5 µL of 4× Detection Mix (Eu-anti-phospho-p70 S6K Antibody 8 nM in 1×LANCE Detection Buffer) were added. The plate was covered with TopSeal-A film and incubated at room temperature for 1h. After the film removal, the signal was read at the Enspire (PerkinElmer) plate reader (excitation 320 nm and emission at 665 nm). The % of enzymatic activity of NEK6 was calculated with respect to the control (100% activity), after subtracting the white of the experiment. For each compound the concentration inhibiting by 50% the activity of NEK6 (IC50) was calculated with software GraphPad Prism5 Software (San Diego, CA, USA).

1.3 Off-Chip Mobility Shift Assay (MSA)

The inhibitory activity on NEK6 of the compounds C8 and C21 was checked with the technique of Off-chip Mobility Shift Assay (MSA) (CARNA Biosciences Study ID: CBS170097, CARNA Biosciences, Kobe). The compounds were dissolved and diluted in DMSO to obtain a concentration 100× and tested at the following dilutions: 100, 30, 10, 3, 1, 0.3, 0.1, 0.03, 0.01, 0.003 µM, in presence of NEK6, 1000 nM peptide CDK7, 5 mM Mg and Km app/Bin: 69/75 µM ATP. PKR inhibitor was used as positive control. 5 mL of solution 4× of the compounds, 5 mL of 4× Substrate/ATP/Metal solution, and 10 mL of 2× kinase solution were prepared with the reaction buffer (20 mM HEPES, 0.01% Triton X-100, 1 mM DTT, pH7.5), mixed and incubated in wells of polypropylene in 384-well plate for 5 hours at room temperature. Afterwards, 70 mL of Termination Buffer (QuickScout Screening Assist MSA; Carna Biosciences) were added. One proceeded with analysing the reaction with LabChip system (Perkin Elmer), by separating and quantizing the peaks of product and substrate. The kinase reaction was then evaluated based upon the ratio (P/(P+S)) calculated based upon the heights of peak of peptides product (P) and substrate (S). The reading value of the control reaction (complete reaction mix) was placed as 0% of inhibition and the bottom value (Enzima (−)) was placed as 100% of inhibition, then the inhibition percentage of each sample was calculated. The value of IC50 was calculated by means of a logistic model at 4 parameters of the inhibition curves by adaptation to a four-parameter logistic curve.

1.4 Analysis of the Expression Levels of NEK6 by Means of Western Blot

The total cell lysates were obtained by incubating the cells in 20 mM Tris-HCl pH 7.4, 5 mM EDTA, 150 mM of sodium chloride, 1% glycerol and 1% Triton X-100, in presence of inhibitors of protease and phosphatase. Forty micrograms of protein lysate were run on gel SDS-PAGE 12% in presence of a marker of molecular weight (Benchmark, Life Technologies, Monza, MB) and transferred on membrane PVDF (Millipore, Bedford, MA). The membrane was incubated for 1 hour with skimmed milk 5% in Tris-buffered saline buffer (Bio-Rad, Hercules, CA), 0.1% Tween-20 (TBST) and subsequently overnight with anti-NEK6 rabbit monoclonal antibody (1:5000, #ab109177 Abcam, Cambridge, UK) in 5% milk, TBST. As charging control the anti-β-actin antibody was used (1:5000, #A5441 Sigma-Aldrich, St. Louis, MO). After 3 15-minute washings in TBST, the membrane was incubated with the secondary antibody conjugated with horseradish peroxidase (Bio-Rad, Hercules, CA) for 1 hour at room temperature. After three subsequent washings in TBST the specific signal for NEK6 was detected with a chemiluminescent system (Amersham Biosciences, Buckinghamshire, UK) by using as image detecting instrument Versadoc (Bio-Rad, Hercules, CA).

1.5 Experiments of Cytotoxicity with the Compounds 8 and 21 in Human Tumour Cell Lines The compounds C8 and C21 identified in the previous assay of enzymatic activity were tested on 8 tumour cell lines representative of different solid tumours: MDA-MB231 and MCF7 (mammary tumour; ATCC, LGC Standards S.r.L, Sesto San Giovanni, MI), PEO1 and COV318 (ovarian tumour; ECACC, Saltssbury, UK), HCT-15 and SW948 (colon tumour; ECAC and ATCC, Sesto San Giovanni, MI), NCI-H1975 and NCI-H1299, (lung tumour; ATCC). Through experiments of cytotoxicity the capability of such compounds of inhibiting the cell growth was evaluated.

The cell lines were kept in culture in 75-cm$^2$ average flasks in atmosphere humidified with 5% CO2/95% air in the following media: DMEM supplemented with 10% FBS, 1% Kanamycin, 1% amino acids not essential for MDA-MB231 and MCF7; RPMI 10% FBS, 1% Kanamycin, 1% amino acids not essential for COV318, NCI-H1975 and NCI-H1299, with addition of 2 mM Sodium Pyruvate for PEO-1; RPMI 20% FBS, 1% Kanamycin, 1% amino acids not essential for HCT-15; LEIBOVITZ'S L15, 10% FBS, 1% Kanamycin, 1% amino acids not essential for SW948. All reagents were purchased at Sigma-Aldrich (St. Louis, MO) if not otherwise specified.

In order to prepare the cytotoxicity experiments the cells were trypsinized, counted with NEUBAUER chamber and plated in black plate having 96 wells per line (Perkinelmer). MDA-MB231, PEO-1, COV318, SW948, NCI-H1975 and NCI-H1299, were plated at 100,000 cells/ml, HCT-15 and MCF-7 at 40,000 cells/ml, In each well of the plate 200 µl of cell suspension were added. 24 h after plating the compounds and/or the drugs were added in quadruplicate at the following concentrations: $6 \times 10^{-6}$ M; $1.2 \times 10^{-5}$ M; $2.4 \times 10^{-5}$ M; $4.8 \times 10^{-5}$ M; $9.6 \times 10^{-5}$ M; $1.92 \times 10^{-4}$ M for C8 (stock solution 10 mM, DMSO100%) and $8 \times 10^{-6}$ M; $1.6 \times 10^{-5}$ M; $3.2 \times 10^{-5}$ M; $6.4 \times 10^{-5}$ M; $1.28 \times 10^{-4}$ M; $2.56 \times 10^{-4}$ M for C21 (stock solution 50 mM, DMSO 100%). Cisplatin (Sigma-Aldrich, St. Louis, MO) was added at the concentrations of $1 \times 10^{-7}$ M; $1 \times 10^{-6}$ M; $2 \times 10^{-6}$ M; $5 \times 10^{-6}$ M; $1 \times 10^{-5}$ M and paclitaxel (Sigma-Aldrich, St. Louis, MO) was added at the concentrations of $1 \times 10^{-9}$ M; $1 \times 10^{-8}$ M; $1 \times 10^{-7}$ M; $1 \times 10^{-6}$ M; $1 \times 10^{-5}$ M. In order to evaluate the synergic effect in PEO-1 the compound 8 was added, at the fixed concentration of IC50, to cisplatin or to paclitaxel. Parallelly, the single curves of each drug and of C8 were performed.

After 72 h from the addition of the compounds and/or drugs, the effect on the cell growth was evaluated by using the kit ATPlite (PerkinElmer) following the manufacturer's specifications. The luminescence signal was read at the instrument ENspire (PerkElmer). For each treated line, the % of inhibition of the growth with respect to the control and IC50 was calculated with software GraphPad Prism5 Software (San Diego, CA, USA). The combination index (CI) was calculated by using the program Compusyn (downloadable from www.combosyn.com), for the analysis of the combined effects of drugs based upon the equation of Chou-Talalay (Chou-Talalay, Adv Enzyme Regul 1984; 22:27-55). CI<1, =1, and >1 designates synergism, additive effect and antagonism, respectively.

2. Results of Experimental Tests

Example 1. In Vitro Evaluation of the Cytotoxic Effect of the Compounds 8 and 21 on MDA-MB231

MDA were plated (100,000 cells/ml) in a 96-well black plate. In each well of the plate 200 µl of cell suspension were added. 24 h after plating the compounds were added in quadruplicate at the following concentrations: C8 (6 µM; 12 µM; 24 µM; 48 µM; 96 µM; 192 µM) and C21 (8 µM; 16 µM; 32 µM; 64 µM; 128 µM; 256 µM). The results illustrated in FIG. 4 and table 1 show that the mammary tumour line MDA-MB231, incubated for 72h with the compound 8 at various scalar dilutions, has an inhibition of the cell growth. The dose of the compound 8 inhibiting 50% (IC50) of the cell growth resulted to be equal to 65±15 µM. Similarly, the compound 21 inhibits the growth by 50% at 75±12 µM.

Example 2. In Vitro Evaluation of the Cytotoxic Effect of the Compounds 8 and 21 on MCF-7

MCF-7 were plated (40,000 cells/ml) in a 96-well black plate. In each well of the plate 200 µl of cell suspension were added. 24 h after plating the compounds were added in quadruplicate at the following concentrations: C8 (6 µM; 12 µM; 24 µM; 48 µM; 96 µM; 192 µM) and C21 (8 µM; 16 µM; 32 µM; 64 µM; 128 µM; 256 µM). The results illustrated in table 1 show that the mammary tumour line MCF-7, incubated for 72h with the compounds 8 and 21 at various scalar dilutions, has no inhibition of the cell growth (IC50>100 µM).

Example 3. In Vitro Evaluation of the Cytotoxic Effect of the Compounds 8 and 21 HCT-15

Figure 5:
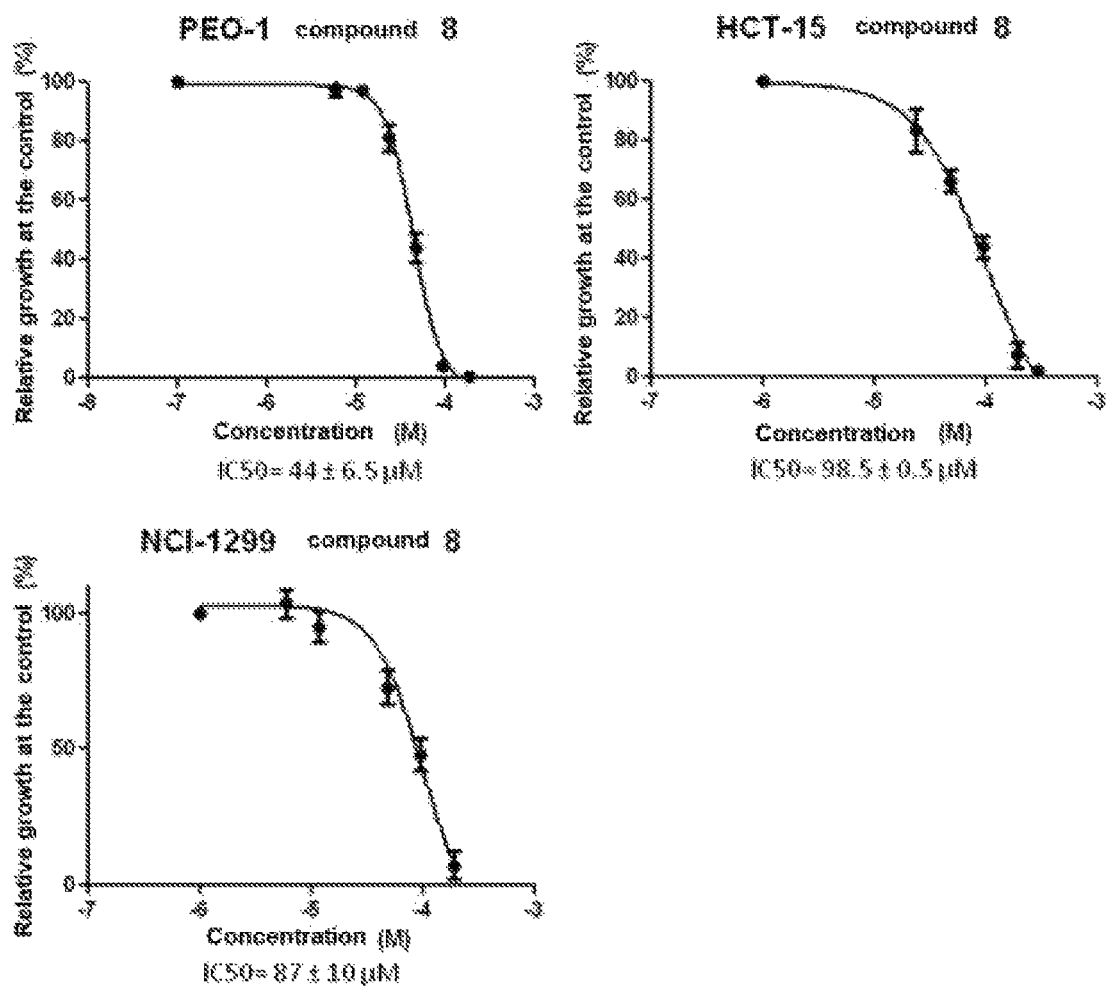
FIG. 5. The graph represents the growth curves of the tumour cell lines PEO-1, HCT-15 and NCI-1299 in presence of growing concentrations of the compound C8. Each point of the curve represents the average±SEM of a quadruplicate of a representative experiment. The value of IC50 was calculated, by considering the average±SEM of at least 2 independent experiments, with the program of statistical analysis Graphpad 5.0.

HCT-15 were plated (40,000 cells/ml) in a 96-well black plate. In each well of the plate 200 µl of cell suspension were added. 24 h after plating the compounds were added in quadruplicate at the following concentrations: C8 (6 µM; 12 µM; 24 µM; 48 µM; 96 µM; 192 µM) and C21 (8 µM; 16 µM; 32 µM; 64 µM; 128 µM; 256 µM). The results illustrated in FIG. 5 show that the colon tumour line HCT-15, incubated for 72h with the compound 8 at various scalar dilutions, has a poor inhibition of the cell growth. The dose of the compound 8 inhibiting by 50% (IC50) the cell growth resulted to be equal to 98.5±0.5 µM. The compound 21 has no inhibitory activity (IC50>100 µM), (Table 1).

Example 4. In Vitro Evaluation of the Cytotoxic Effect of the Compounds 8 and 21 on SW948

SW948 were plated (100,000 cells/ml) in a 96-well black plate. In each well of the plate 200 µl of cell suspension were added. 24 h after plating the compounds were added in quadruplicate at the following concentrations: C8 (6 µM; 12 µM; 24 µM; 48 µM; 96 µM; 192 µM) and C21 (8 µM; 16 µM; 32 µM; 64 µM; 128 µM; 256 µM). The results illustrated in table 1 show that the colon tumour line SW948, incubated for 72h with the compounds 8 and 21 at various scalar dilutions, has no inhibition of the cell growth (IC50>100 µM).

Example 5. In Vitro Evaluation of the Cytotoxic Effect of the Compounds 8 and 21 on COV318

COV318 were plated (100,000 cells/ml) in a 96-well black plate. In each well of the plate 200 µl of cell suspension were added. 24 h after plating the compounds were added in quadruplicate at the following concentrations: C8 (6 µM; 12 µM; 24 µM; 48 µM; 96 µM; 192 µM) and C21 (8 µM; 16 µM; 32 µM; 64 µM; 128 µM; 256 µM). The results illustrated in table 1 show that the ovarian tumour line COV318, incubated for 72h with the compounds 8 and 21 at various scalar dilutions, has no inhibition of the cell growth (IC50>100 µM).

Example 6. In Vitro Evaluation of the Cytotoxic Effect of the Compounds 8 and 21 on PEO-1

PEO-1 were plated (100,000 cells/ml) in a 96-well black plate. In each well of the plate 200 µl of cell suspension were added. 24 h after plating the compounds were added in quadruplicate at the following concentrations: C8 (6 µM; 12 µM; 24 µM; 48 µM; 96 µM; 192 µM) and C21 (8 µM; 16 µM; 32 µM; 64 µM; 128 µM; 256 µM). The results illustrated in FIG. 5 show that the ovarian tumour line PEO-1, incubated for 72 h with the compound 8 at various scalar dilutions, has an inhibition of the cell growth. The dose of the compound 8 inhibiting by 50% (IC50) the cell growth resulted to be equal to 44±6.5 µM. The compound 21 has no inhibitory activity (IC50>100 µM) (Table1).

Example 7. In Vitro Evaluation of the Cytotoxic Effect of the Compounds 8 and 21 on NCI-H1975

NCI-H1975 were plated (100,000 cells/ml) in a 96-well black plate. In each well of the plate 200 µl of cell suspension were added. 24 h after plating the compounds were added in quadruplicate at the following concentrations: C8 (6 µM; 12 µM; 24 µM; 48 µM; 96 µM; 192 µM) and C21 (8 µM; 16 µM; 32 µM; 64 µM; 128 µM; 256 µM). The results illustrated in table 1 show that the lung tumour line NCI-H1975, incubated for 72h with the compounds 8 and 21 at various scalar dilutions, has no inhibition of the cell growth (IC50>100 µM).

Example 8. In Vitro Evaluation of the Cytotoxic Effect of the Compounds 8 and 21 on NCI-H1299

NCI-H1299 were plated (100,000 cells/ml) in a 96-well black plate. In each well of the plate 200 µl of cell suspension were added. 24 h after plating the compounds were added in quadruplicate at the following concentrations: C8 (6 µM; 12 µM; 24 µM; 48 µM; 96 µM; 192 µM) and C21 (8 µM; 16 µM; 32 µM; 64 µM; 128 µM; 256 µM). The results illustrated in FIG. 5 show that the lung tumour line NCI-H1299, incubated for 72h with the compound 8 at various scalar dilutions, has an inhibition of the cell growth. The dose of the compound 8 inhibiting by 50% (IC50) the cell growth resulted to be equal to 87.8±10 µM. The compound 21 has no inhibitory activity (IC50>100 µM), (Table 1).

Example 9. In Vitro Evaluation of the Cytotoxic Effect of the Compound 8 in Combination with Cisplatin in PEO-1

PEO-1 were plated (100,000 cells/ml) in a 96-well black plate. In each well of the plate 200 µl of cell suspension were added. 24 h after plating Cisplatin was added in quadruplicate at the following concentrations: $1 \times 10^{-7}$ M; $1 \times 10^{-6}$ M; $2 \times 10^{-6}$ M; $5 \times 10^{-6}$ M; $1 \times 10^{-5}$ M in combination with the compound 8 at the concentration of IC50 equal to 44 µM. Parallelly, the single curves of Cisplatin and compound 8 were performed. The results illustrated in table 2 show that in the ovarian tumour line PEO-1 the combination Cisplatin+compound 8 has a synergic effect, greater for the combination Cisplatin 10 µM+C8 44 µM (CI=0.69±0.01). The combination index (CI) was calculated by using a program for analysing the combined effects of drugs based upon the equation of Chou-Talalay (Adv Enzyme Regul 1984; 22:27-55), wherein CI<0.1 designates very strong synergism; 0.1-0.3 strong synergism; 0.3-0.7 synergism; 0.7-0.85 moderate synergism; 0.85-0.90 weak synergism; 0.90-1.10 almost additive effect; 1.10-1.20 weak antagonism; 1.20-1.45 moderate antagonism; 1.45-3.3 antagonism; 3.3-10 strong antagonism; >10 very strong antagonism (Chou T C. Pharmacol Rev. 2006; 58:621-81). In particular, the addition of compound 8 to Cisplatin reduces IC50 of Cisplatin in PEO-1 from 7.9±0.65 to 0.1±0.01 µM (Table 3).

Example 10. In Vitro Evaluation of the Cytotoxic Effect of the Compound 8 in Combination with Paclitaxel in PEO-1

PEO-1 were plated (100,000 cells/ml) in a 96-well black plate. In each well of the plate 200 µl of cell suspension were added. 24 h after plating paclitaxel was added in quadruplicate at the following concentrations: $1 \times 10^{-9}$ M; $1 \times 10^{-8}$ M; $1 \times 10^{-7}$ M; $1 \times 10^{-6}$ M; $1 \times 10^{-5}$ M in combination with the compound 8 at the concentration of IC50 equal to 44 µM. Parallelly, the single curves of paclitaxel and compound 8 were performed. The results illustrated in table 4 show that in the ovarian tumour line PEO-1 the combination paclitaxel+compound 8 has a weak synergic effect for the combination paclitaxel $1 \times 10^{-9}$ M+C8 44 µM (CI=0.87±0.023). The combination index (CI) was calculated by using a program for analysing the combined effects of drugs based upon the equation of Chou-Talalay (Adv Enzyme Regul 1984; 22:27-55), wherein CI<0.1 designates very strong synergism; 0.1-0.3 strong synergism; 0.3-0.7 synergism; 0.7-0.85 moderate synergism; 0.85-0.90 weak synergism; 0.90-1.10 almost additive effect; 1.10-1.20 weak antagonism; 1.20-1.45 moderate antagonism; 1.45-3.3 antagonism; 3.3-10 strong antagonism; >10 very strong antagonism (Chou T C. Pharmacol Rev. 2006; 58:621-81). In particular, the addition of compound 8 to paclitaxel reduces 1050 of paclitaxel in PEO-1 from 7.0±0.01 to 0.64±0.057 nM (Table 5).

TABLE 1

In vitro evaluation of the cytotoxic effect of the compounds 8 and 21 on a panel of tumour cell lines.

| Tumour cell lines | IC50 values (µM ± SEM) C8 | IC50 values (µM ± SEM) C21 |
|---|---|---|
| MDA-MB-231 (breast) | 65 ± 15 | 75 ± 12 |
| MCF-7 (breast) | >100 | >100 |
| HCT-15 (colon) | 98.5 ± 0.5 | >100 |
| SW948 (colon) | >100 | >100 |
| PEO-1 (ovary) | 44 ± 6.5 | >100 |
| COV318 (ovary) | >100 | >100 |
| NCI-H1975 (lung) | >100 | >100 |
| NCI-H1299 (lung) | 87.8 ± 10 | >100 |

TABLE 2

In vitro evaluation of the cytotoxic effect of the compound 8 in combination with Cisplatin in the ovarian cancer line PEO-1.

| Cell line | Drug Cisplatin (µM) | Compound 8 (µM) | C.I. (µM ± SEM) | Combination effect |
|---|---|---|---|---|
| PEO-1 | 0.1 | 44 | 0.81 ± 0.08 | Synergism |
|  | 1 | 44 | 1.08 ± 0.26 | Almost additive |
|  | 2 | 44 | 1.01 ± 0.12 | Almost additive |
|  | 5 | 44 | 1.03 ± 0.18 | Almost additive |
|  | 10 | 44 | 0.69 ± 0.01 | Synergism |

C.I < 0.1 Very strong synergism; 0.1-0.3 Strong synergism; 0.3-0.7 Synergism; 0.7-0.85 Moderate synergism; 0.85-0.90 Weak synergism; 0.90-1.10 Almost additive; 1.10-1.20 Weak antagonism; 1.20-1.45 Moderate antagonism; 1.45-3.3 Antagonism; 3.3-10 Strong antagonism; >10 Very strong antagonism.

TABLE 3

IC50 values for the combination cisplatin-compound 8 in PEO-1.

| Drug | IC50 (µM ± SEM) |
|---|---|
| Cisplatin | 7.9 ± 0.65 |
| Cisplatin + C8 (44 µM) | 0.1 ± 0.01 |

TABLE 4

In vitro evaluation of the cytotoxic effect of the compound 8
in combination with paclitaxel in the ovarian cancer line PEO-1.

| Cell line | Drug | | | |
|---|---|---|---|---|
| | Paclitaxel (nM) | Compound 8 (µM) | C.I. (nM ± SEM) | Combination effect |
| PEO-1 | 1 | 44 | 0.87 ± 0.023 | Weak synergism |
| | 10 | 44 | 1.05 ± 0.003 | Almost additive |
| | 100 | 44 | 4.68 ± 0.132 | Strong antagonism |
| | 1000 | 44 | 29.58 ± 0.352 | Very strong antagonism |
| | 10000 | 44 | 287.79 ± 0.001 | Very strong antagonism |

C.I < 0.1 Very strong synergism; 0.1-0.3 Strong synergism; 0.3-0.7 Synergism; 0.7-0.85 Moderate synergism; 0.85-0.90 Weak synergism; 0.90-1.10 Almost additive; 1.10-1.20 Weak antagonism; 1.20-1.45 Moderate antagonism; 1.45-3.3 Antagonism; 3.3-10 Strong antagonism; >10 Very strong antagonism.

TABLE 5

IC50 values for the combination Paclitaxel-compound 8 in PEO-1.

| Drug | IC50 (nM ± SEM) |
|---|---|
| Paclitaxel | 7.0 ± 0.001 |
| Paclitaxel + C8 (44 µM) | 0.64 ± 0.057 |

Table summarizing the binding affinities for NEK6 for all compounds
of formula (A) and (B) calculated by the program Autodock

| Compounds of formula A | | Compounds of formula B | |
|---|---|---|---|
| Compound | Binding affinity (kcal/mol) | Compound | Binding affinity (kcal/mol) |
| A1 (C8) | −7.46 | B1 (C21) | −9.29 |
| A2 | −8.42 | B2 | −9.94 |
| A3 | −8.9 | B3 | −10.63 |
| A4 | −9.38 | B4 | −9.89 |
| A5 | −8.57 | B5 | −9.82 |
| A6 | −8.51 | B6 | −9.78 |
| A7 | −8.2 | B7 | −9.83 |
| A8 | −8.26 | B8 | −9.97 |
| A9 | −8.2 | B9 | −9.91 |
| A10 | −8.28 | B10 | −9.91 |
| A11 | −8.55 | B11 | −9.97 |
| A12 | −8.25 | B12 | −9.79 |
| A13 | −8.44 | B13 | −10.19 |
| A14 | −8.7 | B14 | −10.1 |
| A15 | −9.18 | B15 | −9.92 |

3. Discussion of Results and Definition of Some Terms

Figure 2:
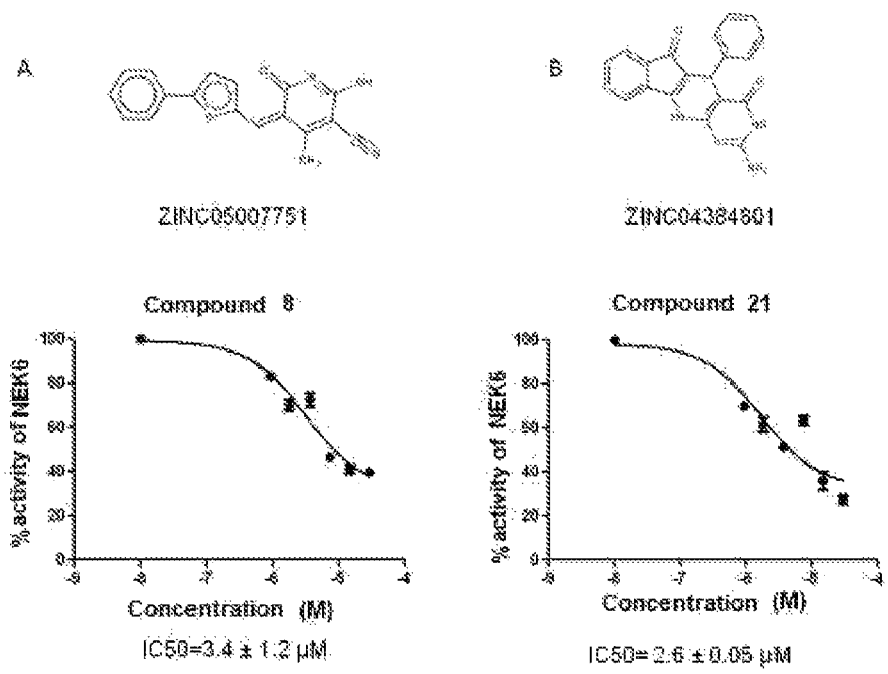
FIG. 2.
Figure 3:
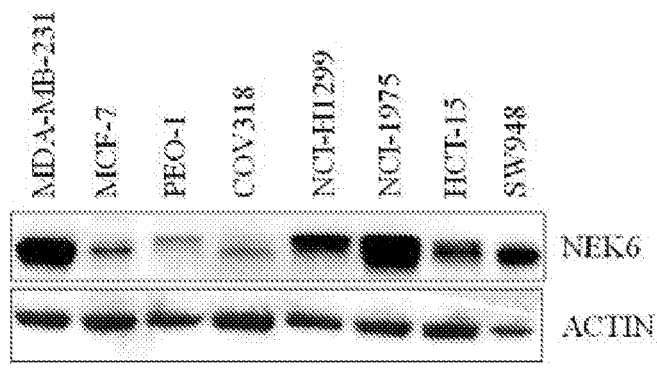
FIG. 3. The western blot shows the expression levels of NEK6 in a panel of tumour cell lines representative of four solid tumours: MDA-MB231 and MCF7 (mammary tumour), PEO1 and COV318 (ovarian tumour), NCI-H1299 and NCI-H1975 (lung tumour), HCT-15 and SW948 (colon tumour). The immunoreaction with actin was used as charging control.
Figure 4:
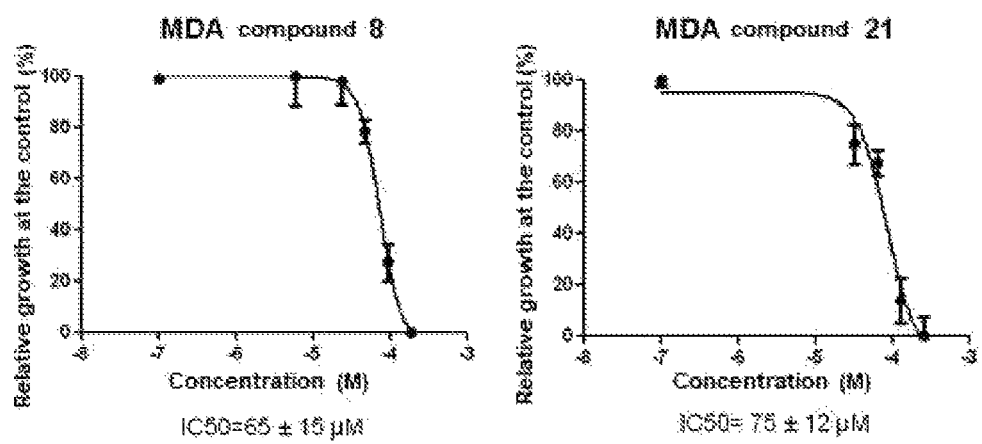
FIG. 4. The graph represents the growth curves of the tumour cell line MDA-MB-231 in presence of growing concentrations of the compounds C8 and C21. Each point of the curve represents the average±SEM of a quadruplicate of a representative experiment. The value of IC50 was calculated, by considering the average±SEM of at least 2 independent experiments, with the program of statistical analysis Graphpad 5.0.

Molecules with different structures were assayed at a single concentration equal to 30 µM in experiments of inhibition of kinase activity of NEK6, by using LANCE technology (FIG. 1). From the initial screening two molecules C8 and C21 were identified, respectively (5Z)-2-hydroxy-4-methyl-6-oxo-5-[(5-phenylfuran-2-yl)methylidene]-5,6-dihydropyridine-3-carbonitrile and 6-amino-2-phenyl-5,7,9-triaza tetracycle[$8.7.0.0^3,^8.0^{11},^{16}$]heptadeca-1(10),3(8),6,11,13,15hexaene-4, 17-dione, having IC50 equal to 3.4±1.2 and 2.6±0.05 µM (IC50±SEM), respectively (FIG. 2). The inhibitory activity of the two compounds on NEK6 was checked with a second method (Off-chip Mobility shift assay) which provided 1050 values equal to 13.8 µM and 49.8 µM for C8 and C21, respectively (CARNA Biosciences Study ID: CBS170097). Afterwards, the selected compounds were tested on a panel of tumour cell lines to evaluate the cytotoxic activity thereof. The expression levels of NEK6 in the used lines are shown in FIG. 3 (FIG. 3). The cells were incubated for 72h with the compounds C8 and C21 at different concentrations, and the cytotoxic effect was determined by measuring the levels of ATP (proportional to the number of vital cells). The results of the cytotoxic experiments show that the compound 8 determines an inhibition of the cell growth in the tumour cell lines of breast (MDA-MB-231), ovary (PEO-1), lung (NCI-H1299) and colon (HCT-15). For each one of these lines IC50 of the compound which gave values lower than 100 µM (FIGS. 4, 5, Table 1) was calculated. The compound 8 did not result to be active in the lines of colon (SW948), breast (MCF-7), ovary (COV318) and lung (NCI-H1975) (IC50>100 µM). The compound 21 showed cytotoxic activity with IC50 lower than 100 µM only in MDA-MB-231, whereas it has not lower activity on other lines (IC50>100 µM) (FIG. 4, Table 1). The obtained results support the development of the two molecules of the derivatives thereof for a customized treatment of neoplastic pathologies.

In the present invention even the combination effect of the compound 8 with antitumour drugs known in the line PEO-1 was evaluated, wherein the compound 8 resulted to be more active. To this purpose, the cells were treated with serial dilutions of cytotoxic drugs (that is cisplatin and paclitaxel) in combination with a fixed dose of C8 (IC50) for 72h. As reference the curves of the single agents were performed. In order to evaluate the cytotoxic activity of the single compounds and of the combination ATP levels were measured. The obtained results show that in the cell line of ovarian tumour PEO-1, the combination cisplatin+inhibitor C8 has a synergic effect (Table 2) with a decrease in IC50 of cisplatin from 7.9±0.65 to 0.1±0.01 µM (Table 3). IC50 value of cisplatin in PEO-1 is according to what reported in literature (3.2±1.4 µM 12.79±1.15 µM) (Wang Q E, et al. Mol Cancer. 2011; 10:24; Stukova M, et al. J Inorg Biochem. 2015; 149:45-8). In PEO-1 a weak synergic effect for the combination paclitaxel+inhibitor C8 at the concentration of paclitaxel 1 nM (Table 4) was further observed. The addition of C8 to paclitaxel determines a decrease in IC50 from 7.0±0.001 nM to 0.64±0.057 nM (Table 5). 1050 value of paclitaxel found in PEO-1 results to be in the range of the values reported in literature (6.5 nM 1050 37 nM) (Fader A N, et al. Anticancer Res. 2010; 30:4791-8; Stukova M, et al. J Inorg Biochem. 2015; 149:45-8). The present invention, led to the identification of two molecular scaffolds active on NEK6 capable of inhibiting the growth of tumour cell lines. The use of such molecules alone or in combination with the currently used chemotherapeutic drugs could determine new therapeutic strategies customized for the patient, ultimately by improving the therapeutic index.

3. Cytotoxicity experiments: experiments allowing to evaluate in vitro the capability of an agent to inhibit the cell growth. The decrease in the number of cells can derive both from stopping proliferation and inducing cell death.

IC50: IC50 or 50 inhibiting concentration, is the concentration of a compound required to inhibit by 50% the target activity under examination with respect to the values measured in absence of inhibitor. IC50 is a parameter used to evaluate the effectiveness of a substance in inhibiting the target and it is one of the methods commonly used in the pharmacological research to measure the power of an antagonist.

Synergism: it is present when the effect of two drugs is higher than the algebraic sum of their single effects. By basing upon the equation of Chou-Talalay (Adv Enzyme Regul 1984; 22:27-55), the combination index (C.I) CI<1, =1, and >1 designates synergism, additive effect and antagonism, respectively.

Therapeutic index: pharmacological parameter indicative of a drug safety. It is defined as the ratio between the average lethal dose and the average effective dose. The higher the ratio is, the higher the relative safety will be. Nowadays more commonly under Therapeutic Index the ratio is meant between the maximum tolerated dose and the minimum effective dose, or by further simplifying, between toxic dose and effective dose.

4. NEK6 is a serine threonine kinase involved in the separation of centrosomes and in keeping the mitotic spindle. It is known that an abnormal function of the centrosomes, deriving from the de-regulated activity of the mitotic kinases, can cause defects of the spindle and abnormal segregations of the chromosomes. This leads to an increase in the genomic instability and to the tumour development.

Even if one does not wish to bind the present invention to any theory, based upon the experiments it can be deduced that the inhibition of NEK6 activity by the compounds C8 and C21 could increase the genomic instability in the tumour cells until levels not compatible with the survival of the same, thus determining a selective cytotoxic effect on the neoplastic cells and not on the normal cells (Dominguez-Brauer C. et al. Mol Cell. 2015; 60:524-36). Besides, several in vitro studies demonstrate that the inhibition of NEK6 activity, through RNA silencing or use of inactive mutants for the kinase activity, determines the mitotic stopping and apoptosis of tumour cells (Fry et al. J Cell Sci 2012; 125:4423-33). In particular Nassirpour and colleagues demonstrated that NEK6 silencing determines an increase in the total expression of BAD and a decrease in the phosphorylation thereof, an increase in the levels of BAX, cutting of caspase-3 and of PARP in several tumour lines. These elements trigger the apoptotic process (Nassirpour et al. Mol Cancer Res. 2010; 8:717-28).

The invention claimed is:

1. A compound according to the general structure formula (A)

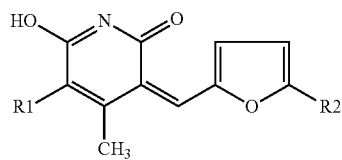

(A)

wherein $R^1$ is a substituent selected from anyone of the following groups

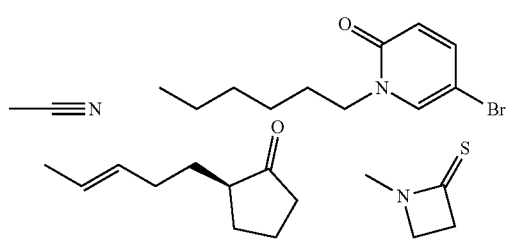

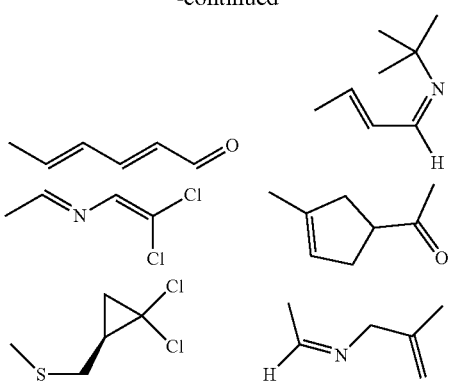

and wherein $R^2$ is a substituent selected from anyone of the following groups:

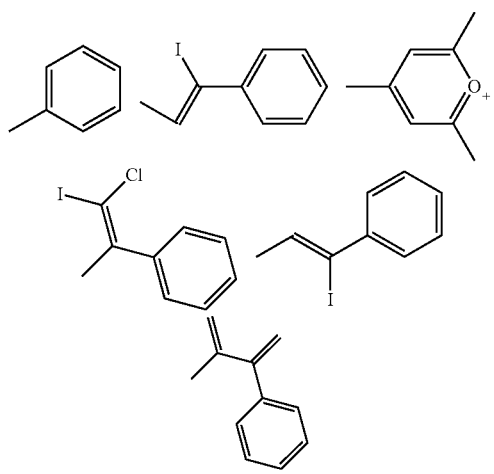

in the form of a racemic mixture or isolated enantiomers, or their salts.

2. The compound of claim 1, selected from one of the following compounds of formula A

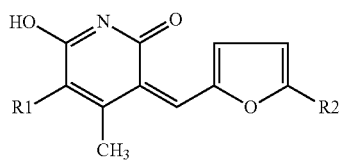

wherein the substituents $R^1$ and $R^2$ are selected according to the formulas A1-A15:

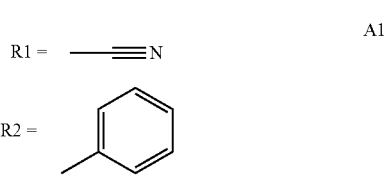

A1

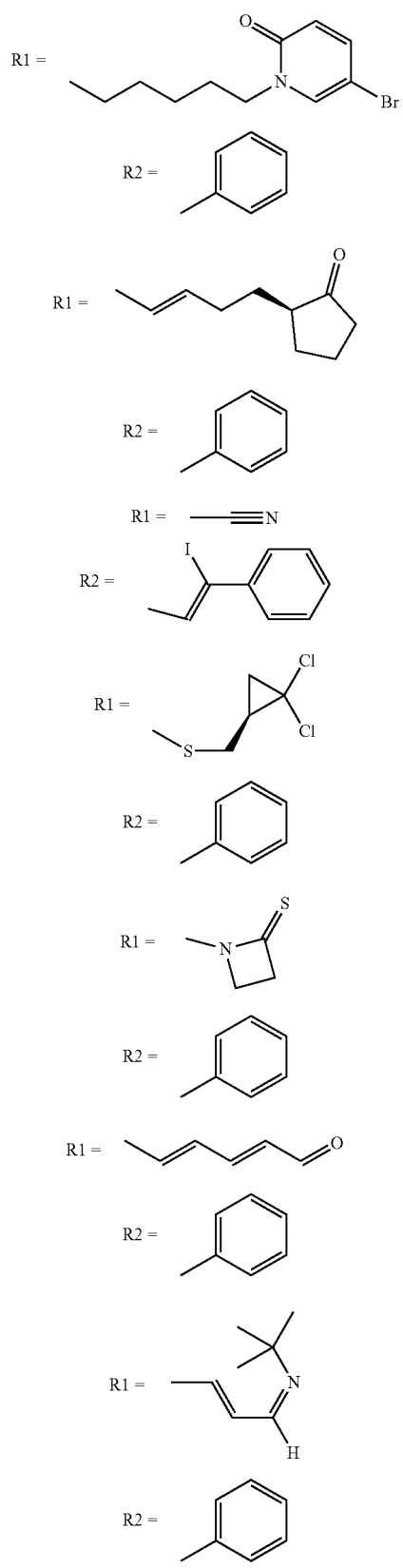
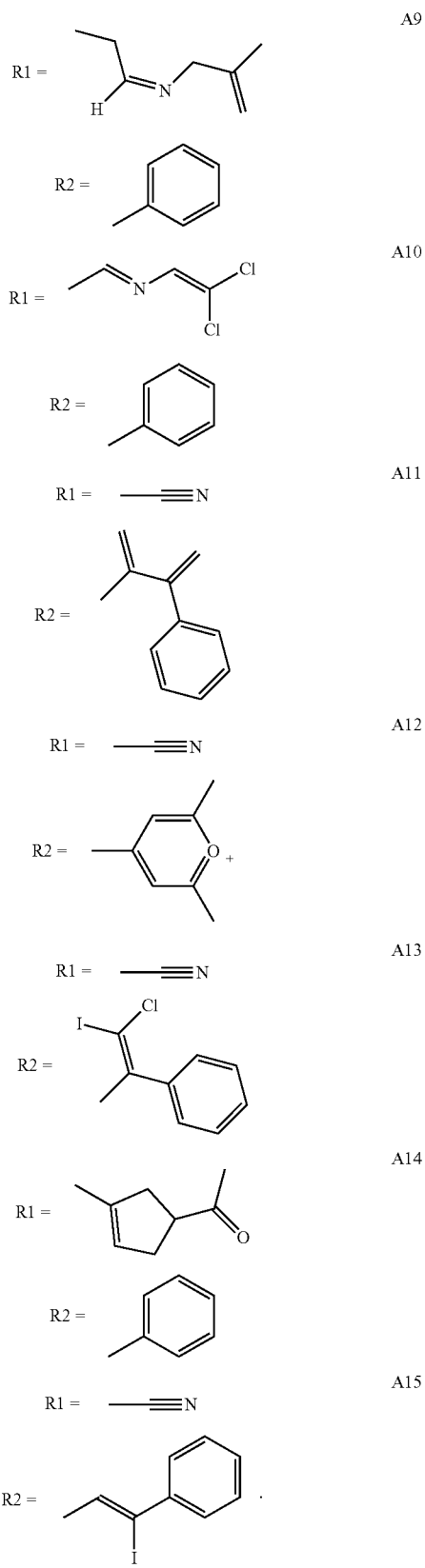
3. The compound of claim 1, wherein said compound has the following structure formula:

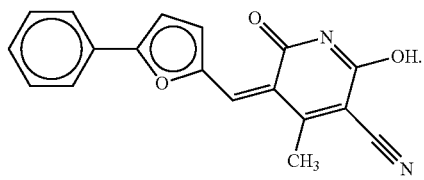

4. A pharmaceutical composition comprising the compound of claim 1 and a pharmaceutically acceptable excipient.

5. The pharmaceutical composition of claim 4 comprising an additional chemotherapeutic agent.

6. The pharmaceutical composition of claim 5, wherein said additional chemotherapeutic agent is paclitaxel or derivatives thereof, drugs belonging to the class of taxanes, cisplatin and platinum-based compounds, or biological antitumor compounds.

7. A kit comprising the compound of claim 1 and a chemotherapeutic drug.

8. A method of inhibiting tumor growth comprising administering a therapeutically effective amount of the compound of claim 1 to a subject in need thereof.

9. The method of claim 8, wherein said tumor is selected from an ovarian tumor, a tumor of the mammary gland, a lung tumor, or a colorectal tumor.

10. The method of claim 8, further comprising administration of a chemotherapeutic agent.

11. A method of inhibiting NEK6 protein kinase activity comprising administering a therapeutically effective amount of the compound of claim 1 to a subject in need thereof.

12. A method of synthesizing the compound of claim 1, comprising the following synthesis steps:

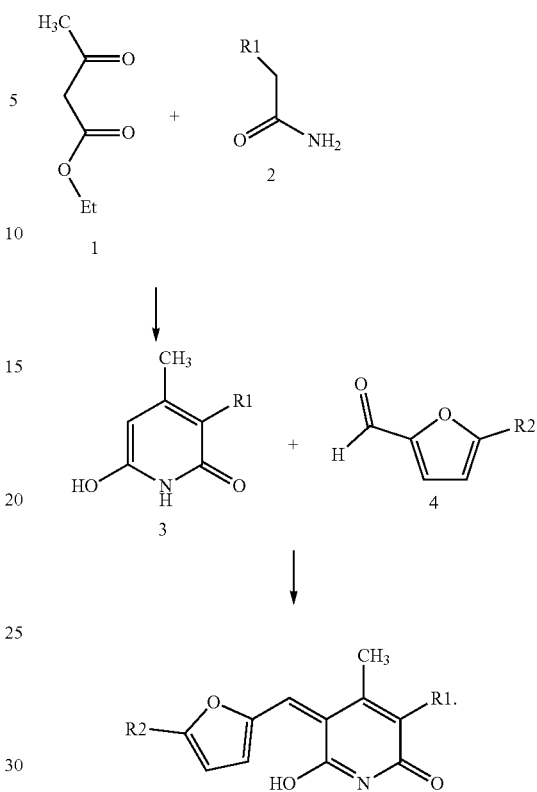

* * * * *